(12) United States Patent
Ghosh

(10) Patent No.: US 8,886,315 B2
(45) Date of Patent: Nov. 11, 2014

(54) EFFECTIVENESS OF VENTRICULAR SENSE RESPONSE IN CRT

(71) Applicant: Medtronic, Inc., Minneapolis, MN (US)

(72) Inventor: Subham Ghosh, Circle Pines, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/706,498

(22) Filed: Dec. 6, 2012

(65) Prior Publication Data

US 2013/0165988 A1 Jun. 27, 2013

Related U.S. Application Data

(60) Provisional application No. 61/579,757, filed on Dec. 23, 2011.

(51) Int. Cl.
| | | |
|---|---|---|
| *A61N 1/08* | (2006.01) | |
| *A61B 5/0452* | (2006.01) | |
| *A61N 1/37* | (2006.01) | |
| *A61B 5/042* | (2006.01) | |
| *A61B 5/00* | (2006.01) | |
| *A61B 5/0464* | (2006.01) | |
| *A61N 1/368* | (2006.01) | |

(52) U.S. Cl.
CPC ............ *A61N 1/3712* (2013.01); *A61B 5/0422* (2013.01); *A61B 5/04525* (2013.01); *A61B 5/0006* (2013.01); *A61B 5/0464* (2013.01); *A61N 1/3684* (2013.01)
USPC ........................................................ 607/28

(58) Field of Classification Search
None
See application file for complete search history.

(56) References Cited

U.S. PATENT DOCUMENTS

| | | | |
|---|---|---|---|
| 4,374,382 A | 2/1983 | Markowitz | |
| 5,117,824 A | 6/1992 | Keimel et al. | |
| 5,545,186 A | 8/1996 | Olson et al. | |
| 5,755,736 A | 5/1998 | Gillberg et al. | |
| 6,381,493 B1 | 4/2002 | Stadler et al. | |
| 6,393,316 B1 | 5/2002 | Gillberg et al. | |
| 7,286,876 B2 | 10/2007 | Yonce et al. | |
| 7,664,550 B2 | 2/2010 | Eick et al. | |
| 7,912,544 B1 | 3/2011 | Min et al. | |
| 7,925,346 B1 | 4/2011 | Go | |

(Continued)

FOREIGN PATENT DOCUMENTS

| | | |
|---|---|---|
| EP | 2 016 976 A1 | 1/2009 |
| EP | 2 188 011 B1 | 5/2011 |

(Continued)

OTHER PUBLICATIONS

Lim, S. Ventricular safety pacing, ventricular sense response, and ventricular tachycardia. Heart Rhythm. Apr. 2010;7(4):567-9.*

(Continued)

*Primary Examiner* — Brian T Gedeon
*Assistant Examiner* — Ankit Tejani
(74) *Attorney, Agent, or Firm* — Carol F. Barry

(57) ABSTRACT

A method for monitoring the effectiveness of VSR and for taking action to improve the effectiveness of VSRs, if they are determined to be ineffective, includes comparing the a VSR evoked electrogram to a template electrogram of a pure biventricular paced CRT beat. If the electrograms, or features thereof, are similar, the VSR is determined to be effective. If the VSR is determined to be ineffective, the AV delay of biventricular CRT is shortened in a step-wise fashion in an incremental manner.

10 Claims, 9 Drawing Sheets

(56) References Cited

U.S. PATENT DOCUMENTS

| | | |
|---|---|---|
| 8,160,700 B1 | 4/2012 | Ryu et al. |
| 2003/0187482 A1 | 10/2003 | Pastore et al. |
| 2004/0220635 A1 | 11/2004 | Burnes |
| 2006/0224198 A1 | 10/2006 | Dong et al. |
| 2009/0005832 A1 | 1/2009 | Zhu et al. |
| 2009/0270937 A1 | 10/2009 | Yonce et al. |
| 2009/0275850 A1* | 11/2009 | Mehendale et al. .......... 600/523 |
| 2009/0318995 A1 | 12/2009 | Keel et al. |
| 2010/0256702 A1* | 10/2010 | Pastore et al. ................... 607/18 |
| 2010/0305461 A1* | 12/2010 | Wei ............................... 600/509 |
| 2011/0022112 A1 | 1/2011 | Min |
| 2011/0054559 A1 | 3/2011 | Rosenberg et al. |
| 2011/0054560 A1 | 3/2011 | Rosenberg et al. |
| 2011/0093031 A1 | 4/2011 | Yu et al. |
| 2012/0185012 A1 | 7/2012 | Ryu et al. |

FOREIGN PATENT DOCUMENTS

| | | |
|---|---|---|
| EP | 2349468 A1 | 9/2011 |
| WO | WO 2005/056108 A2 | 6/2005 |
| WO | WO 2010/039501 A1 | 4/2010 |

OTHER PUBLICATIONS

Gasparini M, et.al. Cardiac resynchronization therapy in heart failure patients with atrial fibrillation. Europace. Nov. 2009;11 Suppl 5:v82-6.*

Hayes et al., "Cardiac Resynchronization Therapy and the Relationship of Percent Biventricular Pacing to Symptoms and Survival," *Heart Rhythm*, 2011, Sep.; 8(9):1469-1475.

International Search Report and Written Opinion issued Jun. 18, 2013, in Europe, Patent Application No. PCT/US2012/070541, filed Dec. 19, 2012; 12 pages.

Kamath et al, "The Utility of 12-Lead Holter Monitoring in Patients with Permanent Atrial Fibrillation for the Identification of Nonresponders After Cardiac Resynchronization Therapy," *Journal of the American College of Cardiology*, 2009, Mar. 24; 53(12): 1050-1055.

Steinhaus BM., "Estimating Cardiac Transmembrane Activation and Recovery Times from Unipolar and Bipolar Extracellular Electrograms: A Simulation Study," *Circulation Research*, 1989, 64:449-462.

* cited by examiner

EFFECTIVENESS OF VENTRICULAR SENSE RESPONSE IN CRT

CROSS-REFERENCE TO RELATED APPLICATIONS

This application claims the benefit of U.S. Provisional Application No. 61/579,757, filed on Dec. 23, 2011. The disclosure of the above application is incorporated herein by reference in its entirety.

FIELD

The present disclosure relates to, among other things, methods, devices and systems for evaluating effectiveness of ventricular sense response and delivering effective pacing in cardiac resynchronization therapy (CRT) devices.

BACKGROUND implantable devices that provide electrical stimulation to selected chambers of the heart have been developed in order to treat a number of cardiac disorders. A pacemaker, for example, is a device which paces the heart with timed pacing pulses, most commonly for the treatment of bradycardia where the ventricular rate is too slow. Implantable devices may also be used to treat cardiac rhythms that are too fast, with either anti-tachycardia pacing or the delivery of electrical shocks to terminate atrial or ventricular fibrillation, Implantable devices have also been developed that affect the manner and degree to which the heart chambers contract during a cardiac cycle in order to promote the efficient pumping of blood. In a properly functioning heart, contraction of each atrium or ventricle is synchronized with the contralateral atrium or ventricle, Without such synchronization, the heart's pumping efficiency is greatly diminished. To treat patients suffering from inefficient or unsynchronized pumping of the heart, CRT devices, which provide appropriately timed electrical stimulation to one or more heart chambers in an attempt to improve the coordination of atrial or ventricular contractions, have been developed.

A common form of CRT applies stimulation pulses to both ventricles, either simultaneously or separated by a specified biventricular offset interval, and after a programmed atrio-ventricular (AV) delay interval with respect to the detection an intrinsic atrial contraction or delivery of an atrial pace. With such CRT, an electrode of a right ventricular lead is placed in contact with the right atrium, typically at the apical wall, and a left ventricular lead containing an electrode for pacing the left ventricle is typically placed in a vein of the coronary sinus overlying the left ventricle.

Typically, it is desirable to pace the ventricles before intrinsic contraction of the ventricles occurs. In cases where an intrinsic ventricular contraction is sensed, a biventricular pacing is often applied soon thereafter, or simultaneously therewith, to produce an effective ventricular contraction. Biventricular pacing on a sensed ventricular contraction is commonly referred to as a ventricular sense response (VSR).

Current CRT devices do not employ a metric for evaluating the efficacy of VSR as compared to standard bi-ventricular pacing. While VSR is intended to generate a composite beat comprising paced and non-paced (intrinsic or otherwise) activation wavefronts, methods for determining the effectiveness of the VSRs are lacking. In general, the less the similarity between the VSR beat and a pure biventricular pacing beat, the less effective the VSR.

SUMMARY

The present disclosure describes, among other things, methods, systems, devices, and the like for monitoring the effectiveness of VSR and for taking action to improve the effectiveness of VSRs.

In embodiments, a method for evaluating the effective of VSR is described herein. The method includes (a) delivering biventricular cardiac resynchronization therapy (CRT) at an atrio-ventricular (AV) interval; (b) monitoring atrial contraction events; (c) monitoring intrinsic ventricular contraction events; (d) applying a biventricular CRT pacing stimulus on detection of an intrinsic ventricular contraction event to produce a ventricular-sense response (VSR); (e) recording electrical activity of the heart in a defined time window centered or off-centered on the time of delivery of the pacing to obtain an electrogram of the VSR (e.g. a time window starting from 50 milliseconds before pacing to 150 milliseconds after pacing); (f) comparing the electrogram of the VSR, or features thereof, to a template electrogram, or features thereof, of a pure biventricular paced beat to determine similarity between the electrogram of the VSR and the template electrogram; (g) determining whether the similarity index meets or exceeds a predetermined threshold, wherein if the similarity index meets or exceeds the threshold steps (a)-(f) are repeated; and (h) determining whether an atrial contraction event preceded the VSR if the threshold is not met or exceeded. In embodiments, the method may further include taking remedial action, which may further include (i) if the atrial contraction event preceded the VSR and the threshold is not met or exceeded, determining whether a preset number of sequentially preceding VSRs were preceded by an atrial contraction event in which the similarity index did not meet or exceed the threshold, wherein if the preset number of sequentially preceding VSRs were not preceded by atrial contraction events in which the similarity index did not meet or exceed the threshold, steps (a)-(h) are repeated; (j) decreasing the AV interval of the CRT by a predetermined amount if the preset number of sequentially preceding VSRs were preceded by atrial contraction events in which the similarity index did not meet or exceed the threshold; and (k) repeating steps (a)-(j) until the similarity index of a VSR meets or exceeds the predetermined threshold in step (g).

In embodiments a computer readable medium for a system configured to deliver cardiac resynchronization therapy is described herein. The computer readable medium comprises instructions that, when implemented, cause the system to: (a) deliver biventricular cardiac resynchronization therapy (CRT) at an atrio-ventricular (AV) interval; (b) monitor atrial contraction events; (c) monitor intrinsic ventricular contraction events; (d) apply a biventricular CRT pacing stimulus on detection of an intrinsic ventricular contraction event to produce a ventricular-sense response (VSR); (e) record electrical activity of the heart in a defined time window centered or off-centered on the time of delivery of the pacing to obtain an electrogram of the VSR; (f) compare the electrogram of the VSR, or features thereof, and a template electrogram, or features thereof, of a pure biventricular paced beat to determine similarity between the electrogram of the VSR and the template electrogram; (g) determine whether the similarity index meets or exceeds a predetermined threshold, and repeat steps (a)-(f) if the similarity index meets or exceeds the threshold; and (h) determine whether an atrial contraction event preceded the VSR if the threshold is not met or exceeded. The computer readable medium may further comprise instructions that when implemented, cause the system to execute the following steps: (i) if the atrial contraction event preceded the VSR and the threshold is not met or exceeded, determine whether a preset number of sequentially preceding VSRs were preceded by an atrial contraction event in which the similarity index did not meet or exceed the threshold, and repeat steps (a)-(h) if the preset number of sequentially preceding VSRs were not preceded by atrial contraction events in which the similarity index did not meet or exceed the threshold; (j) decrease the AV interval of the CRT by a predetermined amount if the preset number of sequentially preceding VSRs were preceded by atrial contraction events in which the similarity index did not meet or exceed the threshold; and (k) repeat steps (a)-(j) until the similarity index of a VSR meets or exceeds the predetermined threshold in step (g). Systems and devices that include the computer-readable medium are also described herein.

One or more of the embodiments of one or more methods, computer readable media, devices or systems described herein may have one or more advantages relative to existing methods, computer readable media, devices or systems for CRT. One of skill in the art will appreciate these advantages upon reading the description and drawings that follow.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

Figure 1:
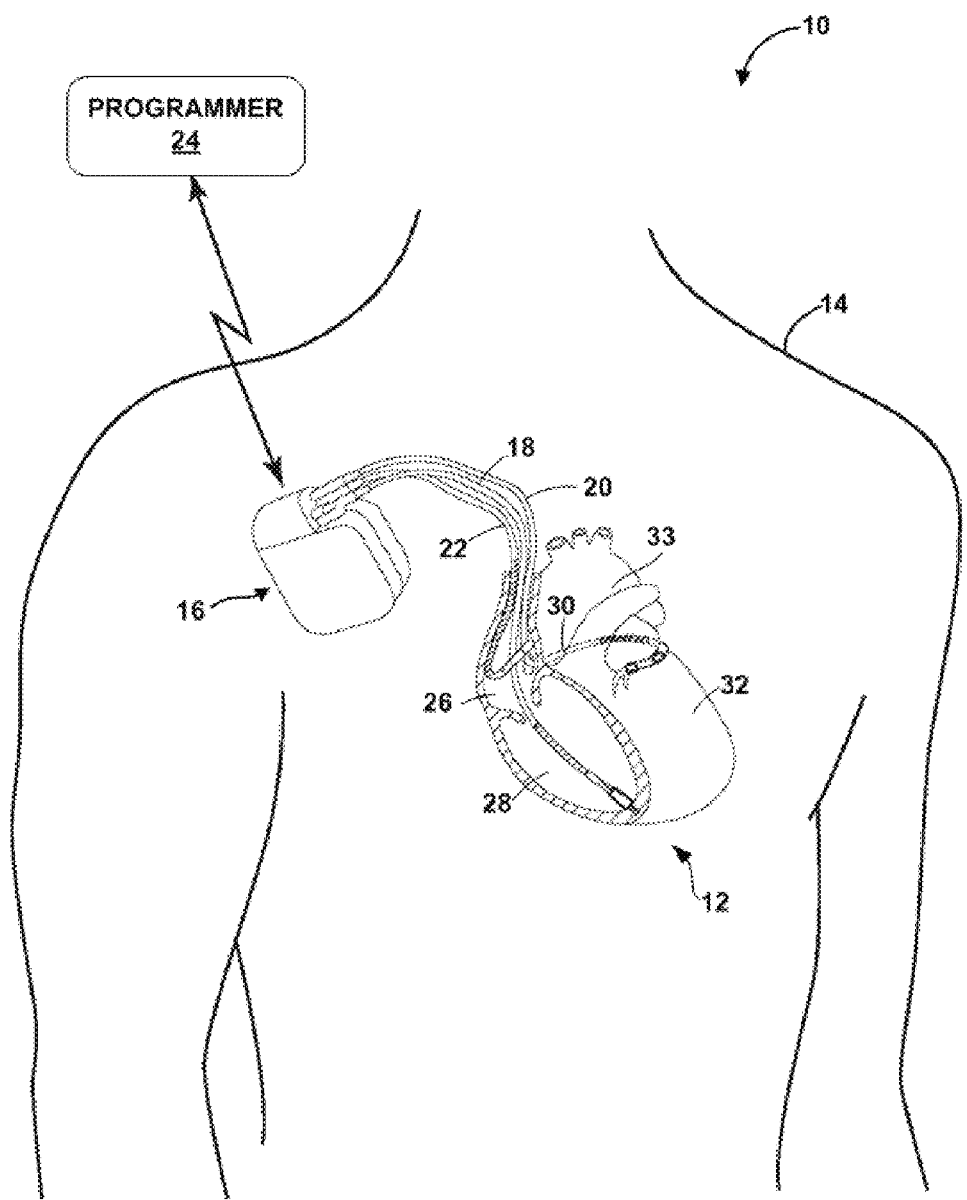
FIG. 1 is a schematic conceptual diagram illustrating an example therapy system that may be used to provide therapy to heart of patient.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

"Consisting essentially of", as it relates to a device, system, or method, means that the device, system, or method includes only the recited components or steps of the device, system, or method and, optionally, other components or steps that do not materially affect the basic and novel properties of the device, system, or methods.

"Consisting of" and "consisting essentially of" are subsumed within "comprising."

Any direction referred to herein, such as "top," "bottom," "left," "right," "upper," "lower," "above," "below," and other directions and orientations are described herein for clarity in reference to the figures and are not to be limiting of an actual device or system or use of the device or system. Many of the devices or systems described herein may be used in a number of directions and orientations.

The present disclosure relates to, among other things, methods, systems, devices, and the like for monitoring the effectiveness of VSR and for taking action to improve the effectiveness of VSRs if they are determined to be ineffective. While many current CRT devices deliver VSR pacing, they do not determine whether the resulting composite beat is effective. In general, the more similar the composite beat resulting from VSR is to a pure biventricular beat, the more effective the VSR beat. Processes for determining effectiveness of VSR that include comparing electrograms, or portions or features thereof, resulting from VSR to electrograms, or portions or features thereof, resulting from pure biventricular pacing are described herein.

In embodiments, the processes described herein include detecting an intrinsic ventricular contraction event and delivering a biventricular pacing stimulus on detection of the ventricular contraction event to produce a VSR. As used herein, "detecting an intrinsic ventricular contraction event," or the like, means detecting electrical activity of the heart, or a portion thereof, that is indicative of a ventricular contraction. Any suitable electrical activity of the heart indicative of a ventricular contraction may be employed. For example, electograms of local electrical activity indicative of ventricular activation may be employed. By way of example, myocardial activation may be detected by monitoring the change in a local electrogram (egm) over time ([egm]/t) to detect electrical activity indicative of activation. Any suitable algorithm for detecting signals indicative of local myocardial activation may be employed. Such algorithms are well known in the art. For example, the algorithms described in Steinhaus B M., 1989, "Estimating cardiac transmembrane activation and recovery times from unipolar and bipolar extracellular electrograms: a simulation study," Circulation Research, 64:449-462 may be used for purposes of detecting myocardial activation and timing of myocardial activation. Global or far field electograms may also be employed for detecting a ventricular contraction event, such as QRS depolarization complex on a surface ECG lead, or the like.

As used herein, delivering or applying a biventricular pacing stimulus "on" detection of the ventricular contraction event means that the biventricular pacing stimulus is applied as soon as practicable following, or simultaneous with, detection of the ventricular contraction event. By delivering the pacing stimulus as soon as possible following initiation of the intrinsic ventricular contraction event, the chances that the VSR beat resembles a pure pacing beat should be improved (relative to delaying pacing). Accordingly, it may be desirable to detect intrinsic ventricular contraction events that are early indicators of ventricular contraction.

In embodiments, the processes include recording electrical activity of the heart in a defined time window in the vicinity of or during VSR pacing (e.g. centered or off-centered on a paced event) to obtain a VSR electrogram. Any suitable time window, such as about 200 milliseconds, may be employed. The VSR electrogram or features thereof may be compared to a template electrogram of a pure biventricular paced beat, or features thereof.

A template electrogram of a pure biventricular paced beat may be obtained in any suitable manner. Preferably, the template is obtained from recordings using the same one or more electrodes that are used for purposes of recording the VSR electrogram. The template electrogram may be obtained following a biventricular CRT pacing stimulus in which no intrinsic ventricular contraction event was detected between pacing events. The template may include a composite of several of such electrograms. The template may be updated periodically or over time.

The VSR electrogram, or features thereof, may be compared to the template electrogram to determine how similar the VSR electrogram, or features thereof, is to a pure biventricular pacing beat. In embodiments, a wavelet matching algorithm, such as an algorithm described in U.S. Pat. No. 6,393,316, is used to determine how similar the VSR electrogram is to the template electrogram. If the VSR electrogram is similar to the template, e.g., 60% or greater similarity, 70% or greater similarity or 80% or greater similarity, the VSR is considered to be effective. If the VSR electrogram is not similar to the template; e.g. less than 60% similarity or less than 70% similarity, the VSR is considered to be ineffective. While wavelet matching is discussed above, it will be understood that other features of the electrograms, such as peaks, slopes, amplitudes, timings, etc., may be compared between the VSR electrogram and the template electrogram to determine whether the feature or features of the VSR are sufficiently similar to the feature or features of the template electrogram to determine that the VSR was effective.

It is believed that long VSR sequences in which ineffective VSR beats are preceded by atrial contraction events, which may be sensed (or intrinsic) or paced events, may lead to a large decrease in the percentage of effective biventricular pacing, which could lead to poor patient response. Accordingly, in embodiments, if the VSR electrogram, or features thereof, are determined to be dissimilar to the template electrogram, a determination is made as to whether an atrial contraction event preceded the VSR.

As used herein, "detection of atrial contraction event," or the like, means detecting electrical activity of the heart, or a portion thereof, that in indicative of an atrial contraction. Any suitable electrical activity of the heart indicative of an atrial contraction may be employed. For example, electograms of local electrical activity indicative of atrial activation may be employed. By way of example, myocardial activation may be detected by monitoring the change in a local electrogram (egm) over time ([egm]/t) to detect electrical activity indicative of activation. Any suitable algorithm for detecting signals indicative of local myocardial activation may be employed. Such algorithms are well known in the art. For example, the algorithms described in Steinhaus B M., 1989, "Estimating cardiac transmembrane activation and recovery times from unipolar and bipolar extracellular electrograms: a simulation study," Circulation Research, 64:449-462 may be used for purposes of detecting myocardial activation and timing of myocardial activation. Global or far field electograms may also be employed for detecting an atrial contraction event, such as presence of P wave or the like In embodiments, if a sufficient number of ineffective VSR beats that were preceded by an atrial event are detected, the AV delay for the biventricular CRT pacing is reduced may a small amount, such as between 5 milliseconds and 20 milliseconds, or about 10 milliseconds. The resulting evoked responses associated with the shortened AV delay may then be compared to the template to see whether the shortening of the AV delay resulted in effective VSR beats. If not, the AV delay may again be shortened by a small amount and the process repeated until effective VSRs are observed. Such incremental small step shortening of the AV delay is intended to ensure that the sensed or paced AV delay is shortened no more than needed to evoke an effective response resembling a pure BV paced response (which may or may not be preceded by a ventricular event; i.e., may or may not be a VSR).

Prior to describing the methods, processes or algorithms for evaluating the effectiveness of VSRs, a discussion of devices and systems for delivering CRT is provided below. A common form of CRT include biventricular CRT, in which both ventricles are stimulated, either simultaneously or separated by a ventricular offset interval, following a programmed atrio-ventricular (AV) delay interval with respect the detection of an intrinsic atrial contraction or delivery of an atrial pace.

1. Overview of Devices and Systems

One exemplary system that may be used for CRT is depicted in the conceptual schematic diagram of FIG. 1. Therapy system 10 of FIG. 1 is configured to provide CRT to heart 12 of patient 14. Patient 12 ordinarily, but not necessarily, will be a human. Therapy system 10 includes an active implantable electrical medical (IMD) 16, which is coupled to leads 18, 20, and 22, and programmer 24. IMD 16 provides electrical signals to, or senses electrical signals from, heart 12 via electrodes coupled to one or more of leads 18, 20, and 22.

In the embodiment depicted in FIG. 1, leads 18, 20, 22 extend into the heart 12 of patient 16 to sense electrical activity of heart 12 or deliver electrical stimulation to heart 12. In the example shown in FIG. 1, right ventricular (RV)

lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12 via a vein branching from the coronary sinus. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. IMD 16 may also provide pacing pulses to heart 12 based on the electrical signals sensed within heart 12. The configurations of electrodes used by IMD 16 for sensing and pacing may be unipolar or bipolar. IMD 16 may, in some embodiments, also provide defibrillation therapy and/or cardioversion therapy via electrodes located on at least one of the leads 18, 20, 22.

Programmer 24 may be a handheld computing device, a computer workstation, or the like. Programmer 24 may include a user interface that receives input from a user. The user interface may include, for example, a keypad and a display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, tachyarrhythmia episodes, or the like. As another example, the user may use programmer 24 to retrieve information from IMD 16 regarding sensed physiological parameters of patient 14, such as intracardiac or intravascular pressure, activity, posture, respiration, thoracic impedance, or the like (if device is so equipped). As another example, the user may use programmer 24 to retrieve information from IMD 16 regarding the performance or integrity of IMD 16 or other components of system 10, such as leads 18, 20, and 22, a power source of IMD 16, or the like.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
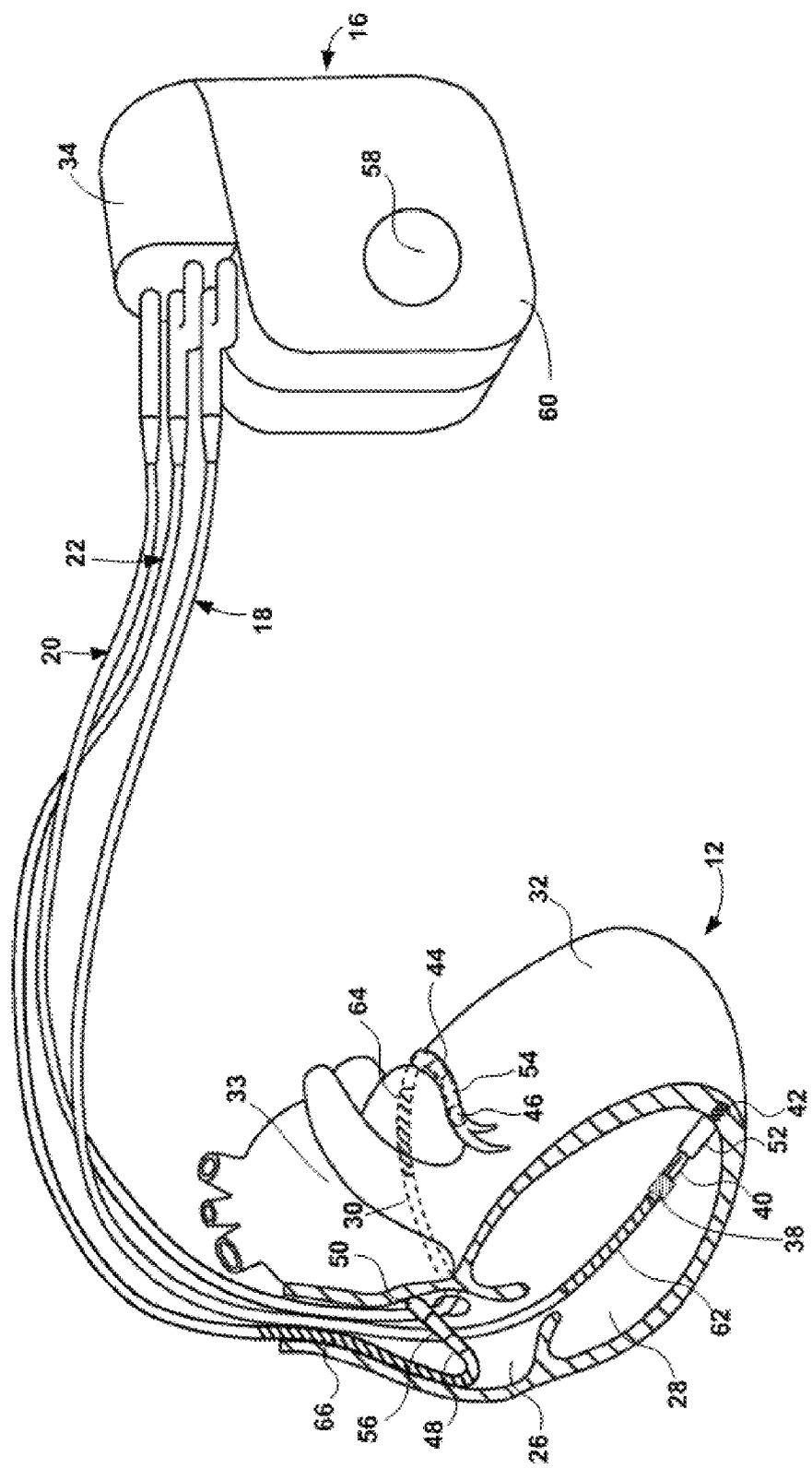
FIG. 2 is a schematic conceptual diagram illustrating an example therapy system that may be used to provide therapy to heart of patient.

FIG. 2 is a conceptual schematic diagram of an embodiment of the system 10 depicted in FIG. 1 illustrating IMD 16 and leads 18, 20, 22 of therapy system 10 in greater detail. Leads 18, 20, 22 may be electrically coupled to a stimulation generator, a sensing module, or other modules IMD 16 via connector block 34. In some examples, proximal ends of leads 18, 20, 22 may include electrical contacts that electrically couple to respective electrical contacts within connector block 34. In addition, in some examples, leads 18, 20, 22 may be mechanically coupled to connector block 34 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. In the illustrated example, an optional pressure sensor 38, such as a capacitive or piezoelectric absolute pressure sensor, and bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22.

Electrodes 40, 44 and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the coiled conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. IMD 16 may also deliver pacing pulses via electrodes 40, 42, 44, 46, 48 and 50 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Any of the electrodes 40, 42, 44, 46, 48 and 50 may be used for unipolar sensing or pacing in combination with housing electrode 58. As described in further detail with reference to FIG. 3, housing 60 may enclose a stimulation generator that generates cardiac pacing pulses, as well as a sensing module for monitoring the patient's heart rhythm.

Leads 18, 20, 22 may also include elongated electrodes 62, 64, 66, respectively, which may take the form of a coil. IMD 16 may deliver defibrillation shocks to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation shocks and other therapies to heart 12 via percutaneous leads that extend through the skin of patient 14 to a variety of positions within or outside of heart 12.

In other examples of therapy systems that provide electrical stimulation therapy to heart 12, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 33. As another example, other examples of therapy systems may include a single lead that extends from IMD 16 into right atrium 26 or right ventricle 28, or two leads that extend into a respective one of the right ventricle 26 and right atrium 28.

For biventricular CRT, IMD 16 applies pacing stimulus via left ventricular lead 20 and right ventricular lead 18, and may apply pacing via atrial lead 22.

Figure 3:
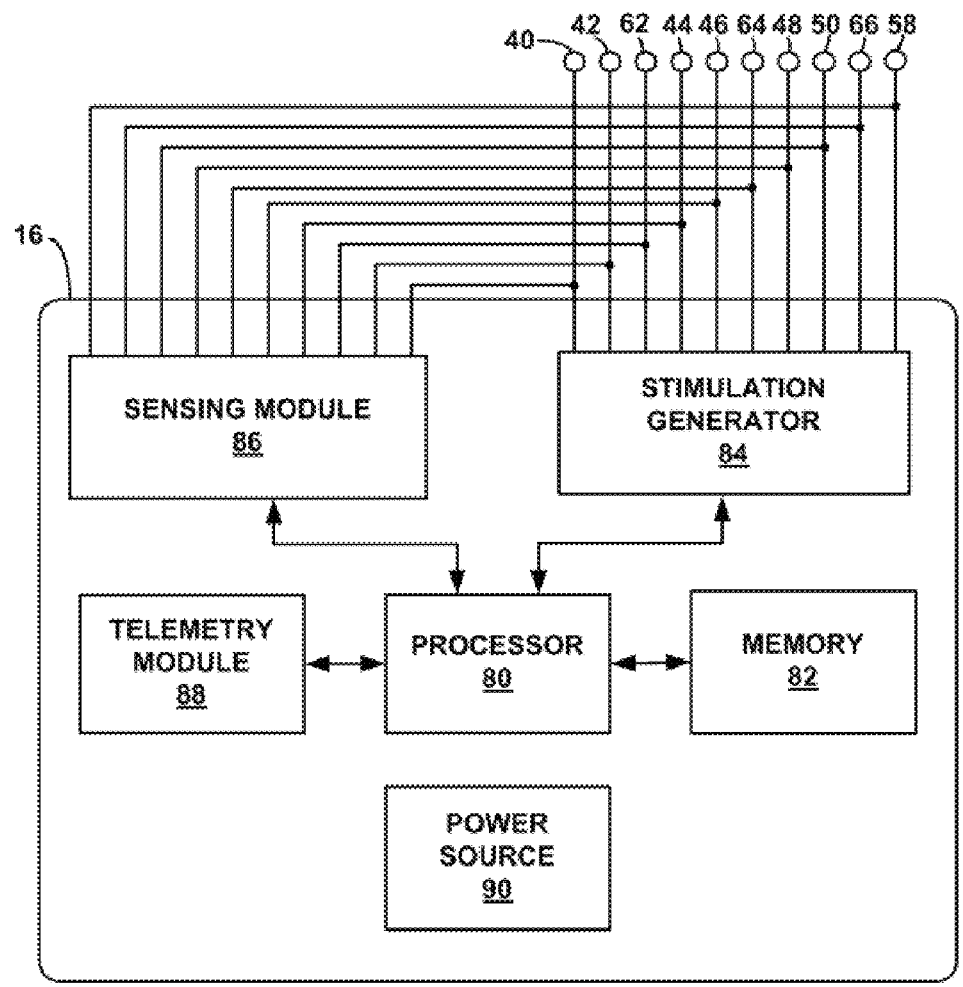
FIG. 3 is a schematic block diagram illustrating some components of an implantable medical device configured to deliver CRT to a patient.

FIG. 3 is a functional block diagram of one example configuration of IMD 16, which includes processor 80, memory 82, stimulation generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls stimulation generator 84 to deliver stimulation therapy to heart 12 according to a selected one or more of therapy programs, which may be stored in memory 82. Specifically, processor 44 may control stimulation generator 84 to deliver electrical pulses with the amplitudes, pulse widths, frequency, or electrode polarities specified by the selected one or more therapy programs.

Stimulation generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Stimulation generator 84 is configured to generate and deliver electrical stimulation therapy to heart 12. For example, stimulation generator 84 may deliver pacing pulses via ring electrodes 40, 44, 48 coupled to leads 18, 20, and 22, respectively, or helical electrodes 42, 46, and 50 of leads 18, 20, and 22, respectively. In some examples, stimulation generator 84 delivers pacing, cardioversion, or defibrillation stimulation in the form of electrical pulses. In other examples, stimulation generator may deliver one or more of these types of stimulation in the form of other signals, such as sine waves, square waves, or other substantially continuous time signals.

Stimulation generator 84 may include a switch module and processor 80 may use the switch module to select, e.g., via a data/address bus, which of the available electrodes are used to deliver defibrillation shocks or pacing pulses. The switch module may include a switch array, switch matrix, multiplexer, or any other type of switching device suitable to selectively couple stimulation energy to selected electrodes.

Sensing module 86 monitors signals from at least one of electrodes 40, 42, 44, 46, 48, 50, 58, 62, 64 or 66 in order to monitor electrical activity of heart 12, e.g., via electrocardiogram (ECG) signals. Sensing module 86 may also include a switch module to select which of the available electrodes are used to sense the heart activity. In some examples, processor 80 may select the electrodes that function as sense electrodes via the switch module within sensing module 86, e.g., by providing signals via a data/address bus. In some examples, sensing module 86 includes one or more sensing channels, each of which may comprises an amplifier. In response to the signals from processor 80, the switch module of within sensing module 86 may couple the outputs from the selected electrodes to one of the sensing channels.

In some examples, one channel of sensing module 86 may include an R-wave amplifier that receives signals from electrodes 40 and 42, which are used for pacing and sensing in right ventricle 28 of heart 12. Another channel may include another R-wave amplifier that receives signals from electrodes 44 and 46, which are used for pacing and sensing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 86 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the heart rhythm of patient 14 by employing any of the numerous signal processing methodologies known in the art.

If IMD 16 is configured to generate and deliver pacing pulses to heart 12, processor 80 may include pacer timing and control module, which may be embodied as hardware, firmware, software, or any combination thereof. The pacer timing and control module may comprise a dedicated hardware circuit, such as an ASIC, separate from other processor 80 components, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within processor 80 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals from sensing module 86 to blank one or more channels, e.g., amplifiers, for a period during and after delivery of electrical stimulation to heart 12. The durations of these intervals may be determined by processor 80 in response to stored data in memory 82. The pacer timing and control module of processor 80 may also determine the amplitude of the cardiac pacing pulses.

During pacing, escape interval counters within the pacer timing/control module of processor 80 may be reset upon sensing of R-waves and P-waves. Stimulation generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may reset the escape interval counters upon the generation of pacing pulses by stimulation generator 84, and thereby control the basic timing of cardiac pacing functions.

The value of the count present in the escape interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as ventricular fibrillation event or ventricular tachycardia event. Upon detecting a threshold number of tachyarrhythmia events, processor 80 may identify the presence of a tachyarrhythmia episode, such as a ventricular fibrillation episode, a ventricular tachycardia episode, a non-sustained tachycardia (NST) episode, or the like.

In some examples, processor 80 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND GREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 80 in other examples.

In the examples described herein, processor 80 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within memory 82 of IMD 16. In addition, the number of tachyarrhythmia events that are detected to confirm the presence of a tachyarrhythmia episode may be stored as a number of intervals to detect (NID) threshold value in memory 82. In some examples, processor 80 may also identify the presence of the tachyarrhythmia episode by detecting a variable coupling interval between the R-waves of the heart signal. For example, if the interval between successive tachyarrhythmia events varies by a particular percentage or the differences between the coupling intervals are higher than a given threshold over a predetermined number of successive cycles, processor 80 may determine that the tachyarrhythmia is present.

If processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by stimulation generator 84 may be loaded by processor 80 into the pacer timing and control module to control the operation of the escape interval counters therein and to define refractory periods during which detection of R-waves and P-waves is ineffective to restart the escape interval counters.

If IMD 16 is configured to generate and deliver defibrillation shocks to heart 12, stimulation generator 84 may include a high voltage charge circuit and a high voltage output circuit. In the event that generation of a cardioversion or defibrillation shock is required, processor 80 may employ the escape interval counter to control timing of such cardioversion and defibrillation shocks, as well as associated refractory periods. In response to the detection of atrial or ventricular fibrillation or tachyarrhythmia requiring a cardioversion pulse, processor 80 may activate a cardioversion/defibrillation control module, which may, like pacer timing and control module, be a hardware component of processor 80 and/or a firmware or software module executed by one or more hardware components of processor 80. The cardioversion/defibrillation control module may initiate charging of the high voltage capacitors of the high voltage charge circuit of stimulation generator 84 under control of a high voltage charging control line.

Processor 80 may monitor the voltage on the high voltage capacitor, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by stimulation generator 84 is controlled by the cardioversion/defibrillation control module of processor 80. Following delivery of the fibrillation or tachycardia therapy, processor 80 may return stimulation generator 84 to a cardiac pacing function and await the next successive interrupt due to pacing or the occurrence of a sensed atrial or ventricular depolarization.

Stimulation generator 84 may deliver cardioversion or defibrillation shocks with the aid of an output circuit that determines whether a monophasic or biphasic pulse is delivered, whether housing electrode 58 serves as cathode or anode, and which electrodes are involved in delivery of the cardioversion or defibrillation shocks. Such functionality may be provided by one or more switches or a switching module of stimulation generator 84.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac episodes that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly basis.

Figure 4:
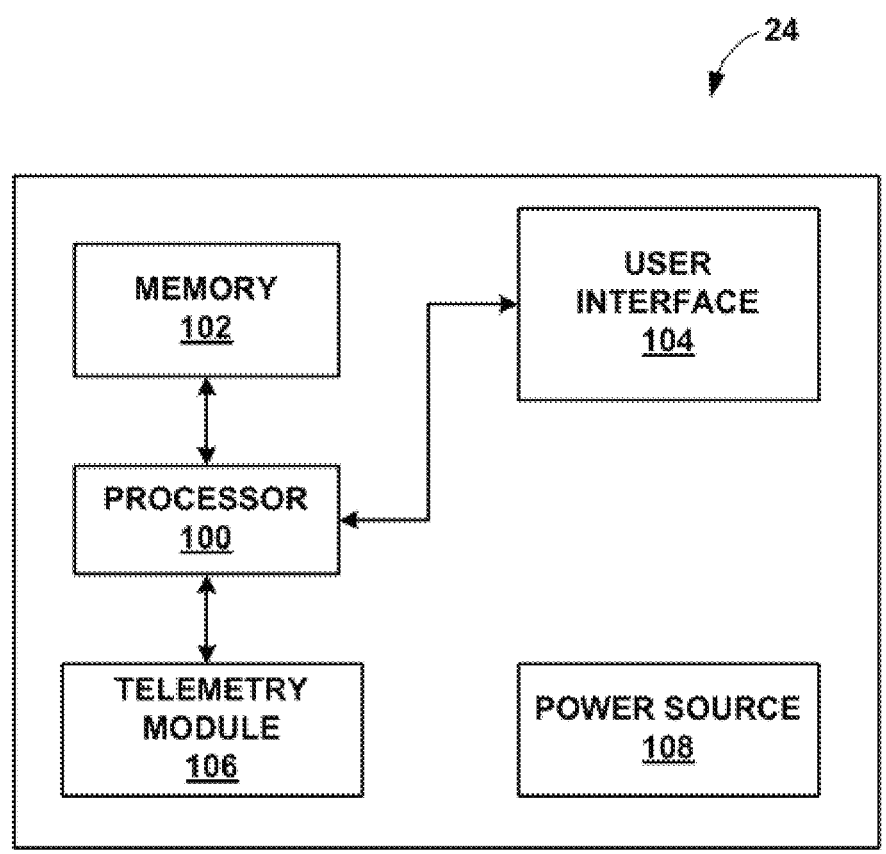
FIG. 4 is a schematic block diagram illustrating some components of a programmer device configured to communicate with an implantable medical device.

FIG. 4 is block diagram of an example programmer 24. As shown in FIG. 4, programmer 24 includes processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 104, which may include display to present graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 102 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient. Memory 102 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 102, which may be coupled to an internal antenna or an external antenna. An external antenna that is coupled to programmer 24 may correspond to the programming head that may be placed over heart 12, as described above with reference to FIG. 1. Telemetry module 102 may be similar to telemetry module 88 of IMD 16 (FIG. 3).

Telemetry module 102 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 108 delivers operating power to the components of programmer 24. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 104 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

Referring again to FIG. 3, processor 80 of IMD 16 may detect a tachyarrhythmia episode, such as a ventricular fibrillation, ventricular tachycardia, fast ventricular tachyarrhythmia episode, a NST episode, or the like, based on electrocardiographic activity of heart 12 that is monitored via sensing module 86. For example, sensing module 86, with the aid of at least some of the electrodes 40, 42, 44, 46, 48, 50, 58, 62, 64, and 66 (shown in FIGS. 1-2), may generate an electrocardiogram (ECG) or electrogram (EGM) signal that indicates the electrocardiographic activity. Alternatively, sensing module 86 may be coupled to sense electrodes that are separate from the stimulation electrodes that deliver electrical stimulation to heart 12 (shown in FIGS. 1-2), and may be coupled to one or more different leads than leads 18, 20, 22 (shown in FIGS. 1-2). The ECG signal may be indicative of the depolarization of heart 12.

For example, as previously described, in some examples, processor 80 may identify the presence of a tachyarrhythmia episode by detecting a threshold number of tachyarrhythmia events (e.g., R-R or P-P intervals having a duration less than or equal to a threshold). In some examples, processor 80 may also identify the presence of the tachyarrhythmia episode by detecting a variable coupling interval between the R-waves of the heart signal.

Figure 5:
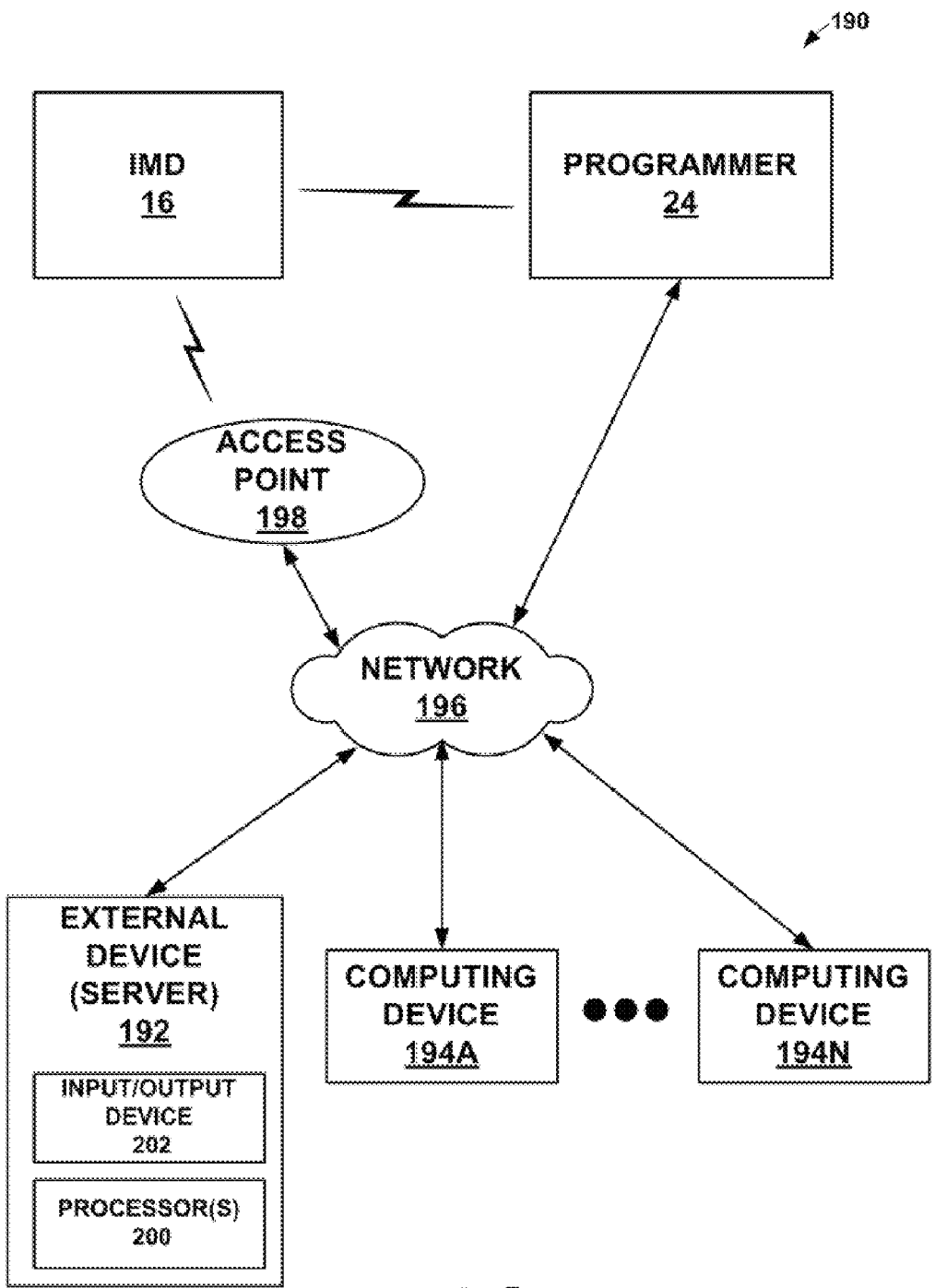
FIG. 5 is a schematic block diagram illustrating a system that includes an external device, such as a server, and one or more computing devices that are coupled to an implantable medical device and programmer via a network.

FIG. 5 is a block diagram illustrating a system 190 that includes an external device 192, such as a server, and one or more computing devices 194A-194N that are coupled to IMD 16 and programmer 24 shown in FIG. 1 via a network 196, according to one embodiment. In this embodiment, IMD 16 uses its telemetry module 88 to communicate with programmer 24 via a first wireless connection, and to communicate with an access point 198 via a second wireless connection. In the example of FIG. 5, access point 198, programmer 24, external device 192, and computing devices 194A-194N are interconnected, and able to communicate with each other, through network 196. In some cases, one or more of access point 198, programmer 24, external device 192, and computing devices 194A-194N may be coupled to network 196 through one or more wireless connections. IMD 16, programmer 24, external device 192, and computing devices 194A-194N may each comprise one or more processors, such as one or more microprocessors, DSPs, ASICs, FPGAs, programmable logic circuitry, or the like, that may perform various functions and operations, such as those described herein.

Access point 198 may comprise a device that connects to network 196 via any of a variety of connections, such as telephone dial-up, digital subscriber line (DSL), or cable modem connections. In other examples, access point 198 may be coupled to network 130 through different forms of connections, including wired or wireless connections. In some examples, access point 198 may communicate with programmer 24 and/or IMD 16. Access point 198 may be co-located with patient 14 (e.g., within the same room or within the same site as patient 14) or may be remotely located from patient 14. For example, access point 198 may be a home monitor that is located in the patient's home or is portable for carrying with patient 14.

During operation, IMD 16 may collect, measure, and store various forms of diagnostic data. In certain cases, IMD 16 may directly analyze collected diagnostic data and generate any corresponding reports or alerts. In some cases, however, IMD 16 may send diagnostic data to programmer 24, access point 198, and/or external device 192, either wirelessly or via access point 198 and network 196, for remote processing and analysis.

In some cases, IMD 16 and/or programmer 24 may combine all of the diagnostic data into a single displayable lead integrity report, which may be displayed on programmer 24. The lead integrity report contains diagnostic information concerning one or more electrode leads that are coupled to IMD 16, such as leads 18, 20, or 22. A clinician or other trained professional may review and/or annotate the lead integrity report, and possibly identify any lead-related conditions.

In another example, IMD 16 may provide external device 192 with collected diagnostic data via access point 198 and network 196. External device 192 includes one or more processors 200. In some cases, external device 192 may request such data, and in some cases, IMD 16 may automatically or periodically provide such data to external device 192. Upon receipt of the diagnostic data via input/output device 202, external device 192 is capable of analyzing the data and generating reports or alerts upon determination that there may be a possible condition with one or more of leads 18, 20, and 22. For example, one or more of leads 18, 20, and 22 may experience a condition related to a lead fracture or an insulation breach.

In one embodiment, external device 192 may combine the diagnostic data into a lead integrity report. One or more of computing devices 194A-194N may access the report through network 196 and display the report to users of computing devices 194A-194N. In some cases, external device 192 may automatically send the report via input/output device 202 to one or more of computing devices 194A-194N as an alert, such as an audio or visual alert. In some cases, external device 192 may send the report to another device, such as programmer 24, either automatically or upon request. In some cases, external device 192 may display the report to a user via input/output device 196.

In one embodiment, external device 192 may comprise a secure storage site for diagnostic information that has been collected from IMD 16 and/or programmer 24. In this embodiment, network 196 may comprise an Internet network, and trained professionals, such as clinicians, may use computing devices 194A-194N to securely access stored diagnostic data on external device 192. For example, the trained professionals may need to enter usernames and passwords to access the stored information on external device 192. In one embodiment, external device 192 may be a CareLink server provided by Medtronic, Inc., of Minneapolis, Minn.

2. Methods and Algorithms

CRT devices and systems; e.g., as described above, may be modified or adapted to monitor the effectiveness of VSR and, in embodiments, to take action to improve the effectiveness of VSRs if they are determined to be ineffective. In many embodiments, the methods or algorithms described herein include comparing evoked VSR responses, or features thereof, to evoked responses, or features thereof, from pure biventricular pacing in which no preceding ventricular contraction event is observed.

Figure 6:
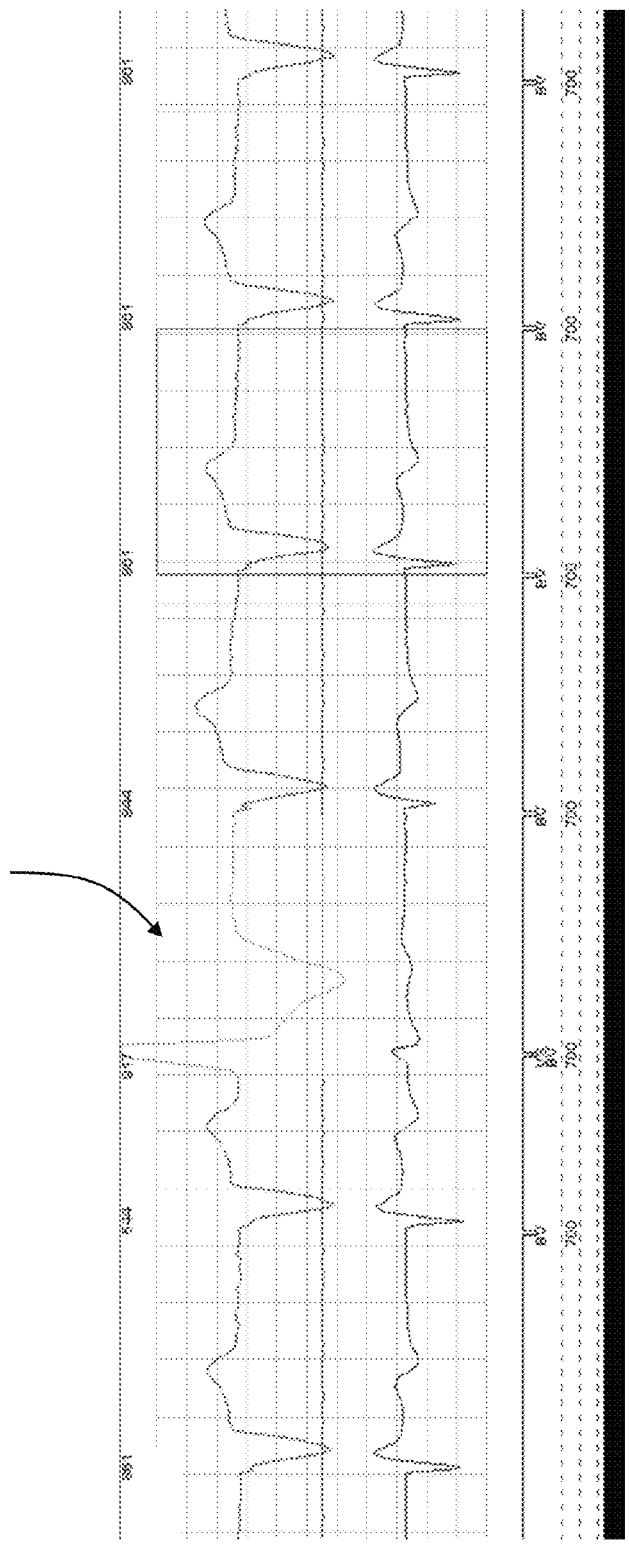
FIG. 6 is a plot of electrograms recorded from a patient receiving biventricular CRT illustrating an ineffective VSR beat, where the top trace is ventricular far-field electrogram (Can/RV Coil) and the bottom trace is ventricular near-field electrogram (RV tip-ring).

Referring to FIG. 6, an example of an ineffective VSR, compared to pure biventricular pacing, is shown. FIG. 6 is a plot of electrograms recorded from a patient receiving biventricular CRT illustrating an ineffective VSR beat (identified by arrow). The example shown is from Holter recordings of a patient with a CRT device. In FIG. 6, the top trace represents ventricular far-field electrogram (Can/RV coil), and the bottom trace represents ventricular near-field electrogram (RV tip-ring). The ineffective VSR beat was determined to have 22% similarity to a pure biventricular pacing beat using a wavelet matching algorithm. The wavelet matching algorithm described earlier in U.S. Pat. No. 6,393,316 involves transforming a signal to be matched to signal wavelet coefficients using a wavelet transform. The higher amplitude wavelet coefficients are identified and compared with those of a template signal by ordering the coefficients according to their absolute amplitude values. A metric of similarity, in terms of an index of percentage match is computed as a result of the comparison. For example, a match percentage >70% may indicate a high degree of similarity between the signal to be matched and the template whereas a lower match percentage may indicate that the signal and the template are dissimilar.

Figure 7:
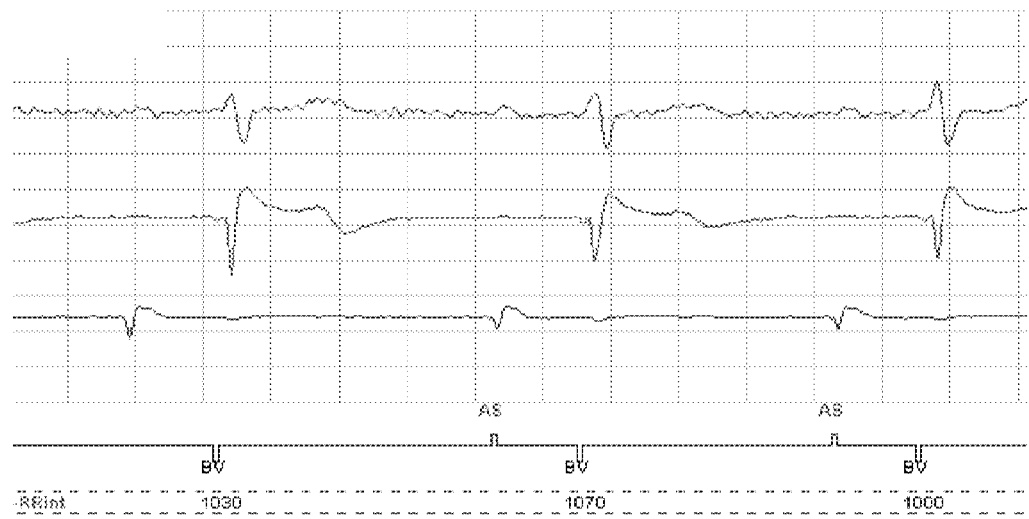
FIG. 7 is a plot of electrograms resulting from pure biventricular pacing, showing a surface ECG lead (top trace), ventricular electrogram (middle trace) and an atrial electrogram (bottom trace) showing atrial sensed events (AS) being detected prior to biventricular pacing (BV).

For purposes of comparison, FIG. 7 shows an electrogram of pure biventricular beats in the same patient from which the recordings in FIG. 6 were obtained. In FIG. 7, the top trace is the ECG signal from a surface lead, the middle trace is the ventricular electrogram, and the bottom trace is the atrial electrogram. As shown in FIG. 7, atrial sensed (AS) events were detected prior to each pure biventricular pacing (BV) event.

Figure 8:
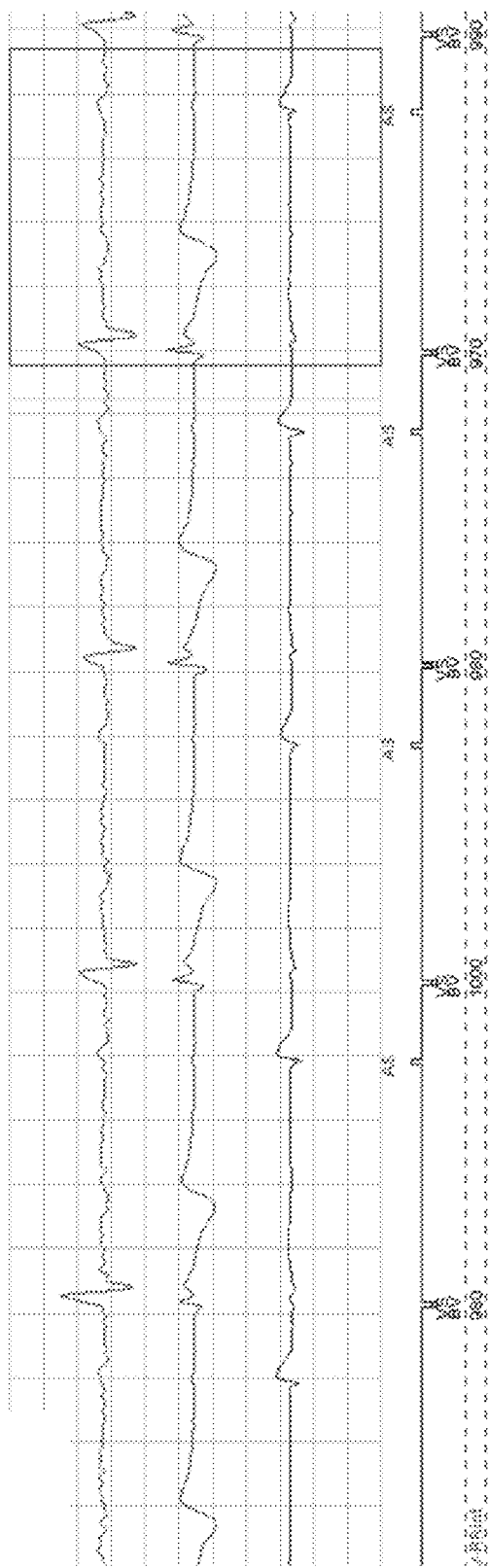
FIG. 8 is a plot of electrograms resulting from VSR pacing, showing a surface ECG lead (top trace) ventricular electrogram(middle trace) and an atrial electrogram (bottom trace) showing atrial sensed events (AS) being detected prior to VSR (VS-BV).

Referring now to FIG. 8, a snap shot from a long duration VSR period where each VSR event is preceded by an atrial event (sensed or paced) is shown. As with FIG. 7, the top trace in FIG. 8 is ECG signal from a surface lead, the middle trace is the ventricular electrogram, and the bottom trace is the atrial electrogram. The wavelet match percent relative to a template of pure biventricular pacing for all beats in FIG. 8 was less than 15%. With the methods described below, corrective action can be taken so that patients receiving CRT, such as the one whose electrogram is depicted in FIG. 8, are not subjected to prolonged periods of ineffective pacing.

Figure 9:
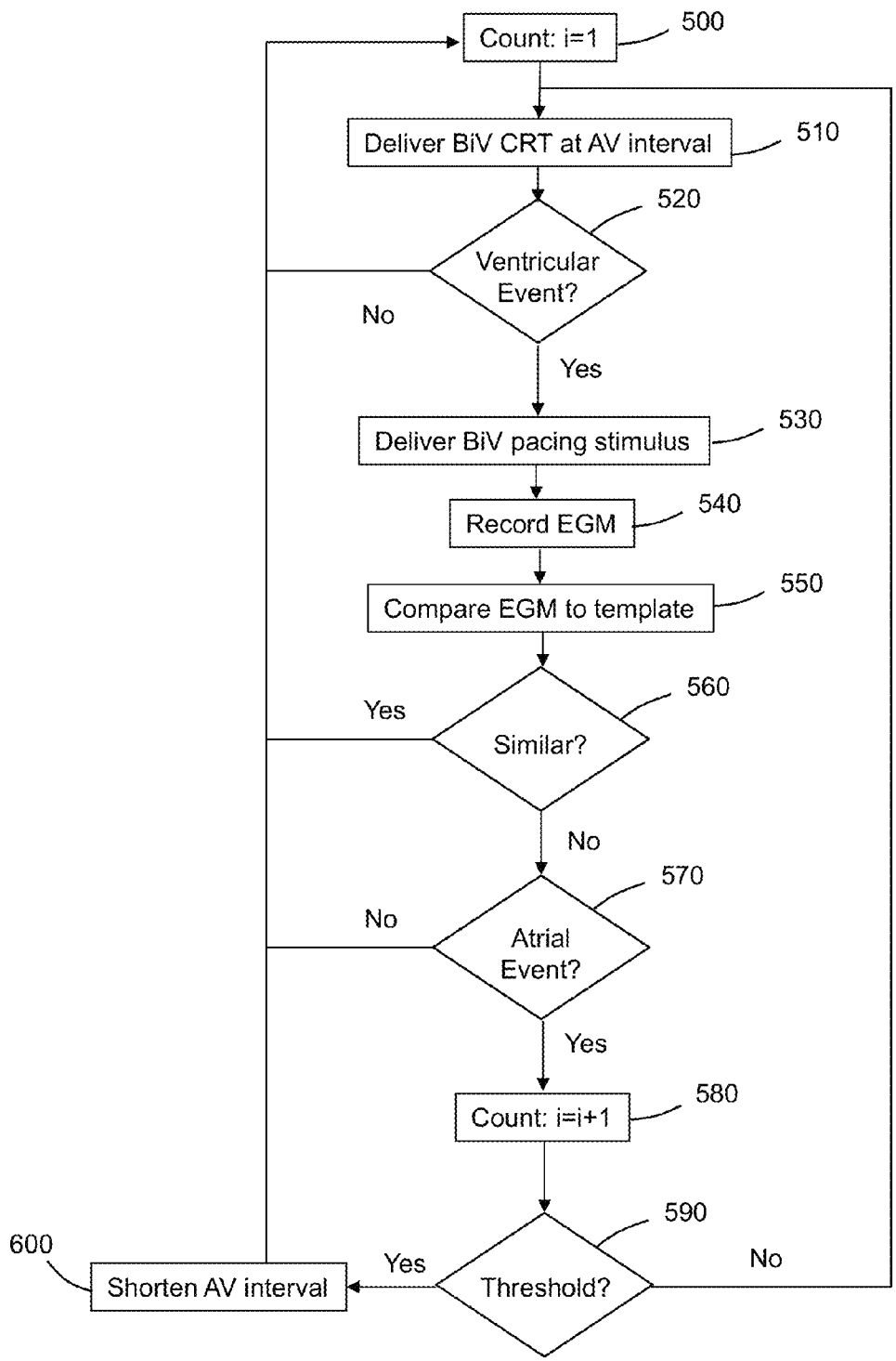
FIG. 9 is a flow diagram illustrating an embodiment of a method described herein.

Referring now to FIG. 9, a method for evaluating the effectiveness of VSR and taking corrective action to avoid prolonged ineffective VSR is shown. As shown, the count of ineffective VSR beats is set at an initial number such as 0 or 1 (500). Biventricular CRT pacing having an initial AV delay may then be delivered to the patient (510). If an intrinsic ventricular contraction event is sensed (520), VSR biventricular pacing is delivered (530) on the detection of the ventricular contraction event. If no intrinsic ventricular contraction event is detected prior to the next scheduled CRT biventricular pacing (510), the count remains at the set number and the CRT pacing is delivered (510). If the VSR biventricular pacing is delivered (530), a VSR evoked electrogram is recorded (540) and compared to a template electrogram from pure biventricular pacing (550), which may be stored in memory. A determination is made as to whether the VSR electrogram, or portions or features thereof, meets or exceeds a predetermined threshold of similarity to the template electrogram, or portions or features thereof (560). Preferably the threshold is set such that the likelihood that a VSR meeting the threshold is an effective beat. If the threshold is met or exceed, the count remain at the set number (500) and the next scheduled CRT biventricular pacing beat is delivered (510) or VSR stimulus is delivered (530) if another intrinsic ventricular contraction event is detected (520).

If the similarity threshold is not met, a determination is made as to whether an atrial contraction event preceded the VSR (570). If no atrial event was detected, the count remains at the set number (500) and the next scheduled CRT biventricular pacing stimulus is delivered (510) or VSR stimulus is delivered (530) if another intrinsic ventricular contraction event is detected (520). If the similarity threshold (560) is not met and an atrial event was determine to precede the VSR (570), the count is increased by 1 (580), and a determination is made as to whether a threshold for sequential VSR events not meeting the similarity threshold and preceded by an atrial event is met (590). The threshold (590) may be set at any number, such as 1, 2, 3, 4, 5, etc. If the threshold (590) is met, the AV delay for the CRT is shortened (600), the count is reset (500) and the process repeated until no intrinsic ventricular events are detected (520) or beats resembling the template (560) are detected. If the threshold (590) is not met, the next scheduled CRT biventricular pacing beat is delivered (510) or VSR stimulus is delivered (530) if another intrinsic ventricular contraction event is detected (520).

It will be understood that the method presented in FIG. 9 is presented for purposes of illustration and that other methods for evaluating effectiveness of VSR and for correcting ineffective VSR are contemplated herein.

The techniques described in this disclosure, including those attributed to IMD, programmer device, or the like, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

A number of embodiments of methods, devices, and systems are described herein. A summary of selected aspects of methods, devices and systems described herein is provided below.

A $1^{st}$ aspect is a method comprising: (a) delivering biventricular cardiac resynchronization therapy (CRT) at an atrio-ventricular (AV) interval; (b) monitoring atrial contraction events; (c) monitoring intrinsic ventricular contraction events; (d) applying a biventricular CRT pacing stimulus on detection of an intrinsic ventricular contraction event to produce a ventricular-sense response (VSR); (e) recording electrical activity of the heart in a defined time window centered or off centered on the time of delivery of the pacing to obtain an electrogram of the VSR; (f)comparing the electrogram of the VSR, or features thereof, to a template electrogram, or features thereof, of a pure biventricular paced beat to determine similarity between the electrogram of the VSR and the template electrogram; (g) determining whether the similarity index meets or exceeds a predetermined threshold, wherein if the similarity index meets or exceeds the threshold steps (a)-(f) are repeated; and (h) determining whether an atrial contraction event preceded the VSR if the threshold is not met or exceeded.

A $2^{nd}$ aspect is a method of the $1^{st}$ aspect, further comprising: (i) if the atrial contraction event preceded the VSR and the threshold is not met or exceeded, determining whether a preset number of sequentially preceding VSRs were preceded by an atrial contraction event in which the similarity index did not meet or exceed the threshold, wherein if the preset number of sequentially preceding VSRs were not preceded by atrial contraction events in which the similarity index did not meet or exceed the threshold, steps (a)-(h) are repeated; (j) decreasing the AV interval of the CRT by a predetermined amount if the preset number of sequentially preceding VSRs were preceded by atrial contraction events in which the similarity index did not meet or exceed the threshold; and (k) repeating steps (a)-(j) until the similarity index of a VSR meets or exceeds the predetermined threshold in step (g).

A 3rd aspect is a method of the 2nd aspect, wherein decreasing the AV interval of the CRT by a predetermined amount in step (j) comprises decreasing the AV delay by between 5 milliseconds and 20 milliseconds.

A 4th aspect is a method of any of aspect 1-3, further comprising: collecting data regarding electrical activity of the heart within a predefined time window from the start of the delivery of the CRT in step (a); verifying no intrinsic ventricular event preceded, or occurred concurrently, with the delivery of the CRT; and forming the template electrogram, or features thereof, from the collected data if no intrinsic ventricular event preceded, or occurred concurrently, with the delivery of the CRT.

A 5th aspect is a method of any of aspects 1-4, wherein monitoring atrial contraction events comprises monitoring atrial sensed events or monitoring atrial paced events.

A 6th aspect is a method of any of aspects 1-5, wherein determining similarity between the electrogram of the VSR and the template electrogram computing a wavelet match percent.

A 7th aspect is a computer readable medium for a system configured to deliver cardiac resynchronization therapy, the computer readable medium comprising instructions that, when implemented, cause the system to: (a) deliver biventricular cardiac resynchronization therapy (CRT) at an atrio-ventricular (AV) interval; (b) monitor atrial contraction events; (c) monitor intrinsic ventricular contraction events; (d) apply a biventricular CRT pacing stimulus on detection of an intrinsic ventricular contraction event to produce a ventricular-sense response (VSR); (e) record electrical activity of the heart in a defined time window centered or off centered on the time of delivery of the pacing to obtain an electrogram of the VSR; (f) compare the electrogram of the VSR, or features thereof, and a template electrogram, or features thereof, of a pure biventricular paced beat to determine similarity between the electrogram of the VSR and the template electrogram; (g) determine whether the similarity index meets or exceeds a predetermined threshold, and repeat steps (a)-(f) if the similarity index meets or exceeds the threshold; and (h) determine whether an atrial contraction event preceded the VSR if the threshold is not met or exceeded.

An 8th aspect is a computer readable medium of the 7th aspect, further comprising instructions that when implemented, cause the system to: (i) if the atrial contraction event preceded the VSR and the threshold is not met or exceeded, determine whether a preset number of sequentially preceding VSRs were preceded by an atrial contraction event in which the similarity index did not meet or exceed the threshold, and repeat steps (a)-(h) if the preset number of sequentially preceding VSRs were not preceded by atrial contraction events in which the similarity index did not meet or exceed the threshold; (j) decrease the AV interval of the CRT by a predetermined amount if the preset number of sequentially preceding VSRs were preceded by atrial contraction events in which the similarity index did not meet or exceed the threshold; and (k) repeat steps (a)-(j) until the similarity index of a VSR meets or exceeds the predetermined threshold in step (g).

A 9th aspect is a system comprising: (i) the computer readable medium of aspect 7 or 8; (ii) electronics capable of executing the instructions of the computer readable medium; (iii) one or more electrodes to deliver the CRT of steps (a) and (d); and (iv) one or more electrodes configured to monitor the atrial contractions events in step (a), monitor the intrinsic ventricular contraction events in step (c), record the electrical activity of the heart in step (e).

A 10th aspect is a device comprising: (i) the computer readable medium of claim 7 or 8; (ii) a processor capable of executing the instructions of the computer readable medium; (iii) one or more pacing circuits configured to deliver the CRT of steps (a) and (d); and (iv) one or more sensing circuits configured to monitor the atrial contractions events in step (a), monitor the intrinsic ventricular contraction events in step (c), record the electrical activity of the heart in step (e).

Thus, systems, devices, computer-readable media and methods for EFFECTIVENESS OF VENTRICULAR SENSE RESPONSE IN CRT are described. Those skilled in the art will recognize that the preferred embodiments described herein may be altered or amended without departing from the true spirit and scope of the disclosure, as defined in the accompanying claims.

The invention claimed is:
1. A method comprising:
(a) delivering biventricular cardiac resynchronization therapy (CRT) to a heart at an atrio-ventricular (AV) interval;
(b) monitoring atrial contraction events;
(c) monitoring intrinsic ventricular contraction events;
(d) applying a biventricular CRT pacing stimulus on detection of an intrinsic ventricular contraction event to produce a ventricular-sense response (VSR);
(e) recording electrical activity of the heart in a defined time window centered or off centered on a time of delivery of the biventricular CRT pacing stimulus to obtain an electrogram of the VSR;
(f) comparing the electrogram of the VSR, or features thereof, to a template electrogram, or features thereof, of a pure biventricular paced beat to determine a similarity index between the electrogram of the VSR and the template electrogram;
(g) determining whether the similarity index meets or exceeds a predetermined threshold, wherein if the similarity index meets or exceeds the threshold steps (a)-(f) are repeated; and
(h) determining whether an atrial contraction event preceded the VSR if the threshold is not met or exceeded.

2. The method of claim 1, further comprising:
(i) if the atrial contraction event preceded the VSR and the threshold is not met or exceeded, determining whether a preset number of sequentially preceding VSRs were preceded by an atrial contraction event in which the similarity index did not meet or exceed the threshold,
wherein if the preset number of sequentially preceding VSRs were not preceded by atrial contraction events in which the similarity index did not meet or exceed the threshold, steps (a)-(h) are repeated;
(j) decreasing the AV interval of the CRT by a predetermined amount if the preset number of sequentially preceding VSRs were preceded by atrial contraction events in which the similarity index did not meet or exceed the threshold; and
(k) repeating steps (a)-(j) until the similarity index of a VSR meets or exceeds the predetermined threshold in step (g).

3. The method of claim 2, wherein the decreasing the AV interval of the CRT by a predetermined amount in step (j) comprises decreasing the AV interval by between 5 milliseconds and 20 milliseconds.

4. The method of any of claims 1-3, further comprising:
collecting data regarding electrical activity of the heart within a predefined time window from a start of the delivery of the CRT in step (a);
verifying no intrinsic ventricular event preceded, or occurred concurrently, with the delivery of the CRT; and
forming the template electrogram, or features thereof, from the collected data if no intrinsic ventricular event preceded, or occurred concurrently, with the delivery of the CRT.

5. The method claim 1, wherein the monitoring atrial contraction events comprises monitoring atrial sensed events or monitoring atrial paced events.

6. The method of claim 1, wherein the determining of a similarity index between the electrogram of the VSR and the template electrogram comprises computing a wavelet match percent.

7. A non-transitory computer readable medium for a system configured to deliver cardiac resynchronization therapy, the computer readable medium comprising instructions that, when implemented, cause the system to:
(a) deliver biventricular cardiac resynchronization therapy (CRT) to a heart at an atrio-ventricular (AV) interval;
(b) monitor atrial contraction events;
(c) monitor intrinsic ventricular contraction events;
(d) apply a biventricular CRT pacing stimulus on detection of an intrinsic ventricular contraction event to produce a ventricular-sense response (VSR);
(e) record electrical activity of the heart in a defined time window centered or off centered on a time of delivery of the biventricular CRT pacing stimulus to obtain an electrogram of the VSR;
(f) compare the electrogram of the VSR, or features thereof, and a template electrogram, or features thereof, of a pure biventricular paced beat to determine a similarity index between the electrogram of the VSR and the template electrogram;
(g) determine whether the similarity index meets or exceeds a predetermined threshold, and repeat steps (a)-(f) if the similarity index meets or exceeds the threshold; and
(h) determine whether an atrial contraction event preceded the VSR if the threshold is not met or exceeded.

8. The computer readable medium of claim 7, further comprising instructions that when implemented, cause the system to:
(i) if the atrial contraction event preceded the VSR and the threshold is not met or exceeded, determine whether a preset number of sequentially preceding VSRs were preceded by an atrial contraction event in which the similarity index did not meet or exceed the threshold, and repeat steps (a)-(h) if the preset number of sequentially preceding VSRs were not preceded by atrial contraction events in which the similarity index did not meet or exceed the threshold;
(j) decrease the AV interval of the CRT by a predetermined amount if the preset number of sequentially preceding VSRs were preceded by atrial contraction events in which the similarity index did not meet or exceed the threshold; and
(k) repeat steps (a)-(j) until the similarity index of a VSR meets or exceeds the predetermined threshold in step (g).

9. A system comprising:
the computer readable medium of claim 7 or 8;
electronics capable of executing the instructions of the computer readable medium;
one or more electrodes to deliver the CRT of steps (a) and (d); and
one or more electrodes configured to monitor the atrial contractions events in step (a), monitor the intrinsic ventricular contraction events in step (c), record the electrical activity of the heart in step (e).

10. A device comprising:
the computer readable medium of claim 7 or 8;
a processor capable of executing the instructions of the computer readable medium;
one or more pacing circuits configured to deliver the CRT of steps (a) and (d); and
one or more sensing circuits configured to monitor the atrial contractions events in step (a), monitor the intrinsic ventricular contraction events in step (c), record the electrical activity of the heart in step (e).

* * * * *